United States Patent [19]

Horodysky et al.

[11] Patent Number: 4,661,271
[45] Date of Patent: Apr. 28, 1987

[54] FRICTION REDUCING, ANTIWEAR ADDITIVES

[75] Inventors: Andrew G. Horodysky, Cherry Hill; Henry Ashjian, E. Brunswick, both of N.J.

[73] Assignee: Mobil Oil Corporation, New York, N.Y.

[21] Appl. No.: 639,180

[22] Filed: Aug. 9, 1984

[51] Int. Cl.$^4$ ............................................ C10M 137/00
[52] U.S. Cl. ................................... 252/32.5; 548/347
[58] Field of Search ........................ 252/32.5; 548/347

[56] References Cited

U.S. PATENT DOCUMENTS

| | | | |
|---|---|---|---|
| 3,159,664 | 12/1964 | Bartlett | 252/49.8 |
| 3,720,612 | 3/1973 | Bosniack et al. | 252/32.5 |
| 3,932,287 | 1/1976 | Schneider | 252/32.5 |
| 4,052,324 | 10/1977 | Braid | 252/32.5 |
| 4,089,793 | 5/1978 | Meinhardt | 252/32.5 |
| 4,125,472 | 11/1978 | Braid | 252/32.5 |
| 4,130,494 | 12/1978 | Shaub | 252/32.5 |
| 4,144,180 | 3/1979 | Andress, Jr. | 252/32.5 |
| 4,177,154 | 12/1979 | Chakrabarti | 252/32.3 |
| 4,210,542 | 7/1980 | Mann | 252/32.5 |
| 4,216,334 | 8/1980 | Jones | 252/32.5 |

*Primary Examiner*—William R. Dixon, Jr.
*Assistant Examiner*—Cynthia A. Prezlock
*Attorney, Agent, or Firm*—Alexander J. McKillop; Michael G. Gilman; Howard M. Flournoy

[57] ABSTRACT

Imidazoline salts of acid phosphates derived from hydrocarbyl diols or mixtures of hydrocarbyl diols are effective multifunctional friction reducing additives when incorporated into various fluid hydrocarbyl compositions.

13 Claims, No Drawings

FRICTION REDUCING, ANTIWEAR ADDITIVES

BACKGROUND OF THE INVENTION

This invention is directed to lubricant additives and compositions thereof, and more particularly to liquid hydrocarbyl fuels and lubricant compositions, comprising said fuels or oils of lubricating viscosity or greases prepared therefrom containing friction reducing amounts of imidazoline salts of acid phosphates derived from hydrocarbyl diols or mixtures thereof.

Phosphorus-containing additives have been extensively used in lubricant applications. These additives include phosphites, phosphate esters, acid phosphates, phosphonates, metallic dithiophosphates and the like.

Imidazolines have found use as friction reducing additives as described in U.S. Pat. Nos. 4,394,278 and 4,298,486. U.S. Pat. No. 4,427,562 discloses imidazolines and certain esters thereof as known antifriction additives. U.S. Pat. No. 4,163,731 is directed to certain fire resistant functional fluids based on phosphate esters and substituted aromatic compounds, as for example, heterocyclic compounds such as imidazolines.

Hydroxy-containing additives and their derivatives are well-known for their water scavenging properties when formulated into fuels and for their lubricity characteristics when blended into lubricants. The use of glycerol monooleate and similar hydroxyl-containing carboxylates have found wide spread commercial use as lubricant additives. The use of related diols is described in U.S. Pat. Nos. 3,649,358 and 3,899,433.

The hydrocarbyl-diol derived imidazoline salts of acid phosphates as disclosed herein contribute excellent friction reducing properties when formulated at low additive concentrations into hydrocarbyl fuels, fluid lubricants and greases. The modest acid phosphate content provides the basis for significant synergistic wear activity in the highly surface active molecules of the embodied products. The basis for antirust and anticorrosion properties is provided by the nitrogen-containing heterocyclic moiety, particularly the imidazoline-containing acid phosphates.

To the best of applicants' knowledge and belief, both the additive structures per se and the lubricant compositions containing such additives are novel. Further, the unique compositions disclosed herein are not known to have been previously used as multifunctional friction reducing antiwear or antirust additives in hydrocarbyl lubricating oils, greases, or fuels.

SUMMARY OF THE INVENTION

In accordance with the invention, there is provided additive products comprising various imidazoline salts of diol-derived acid phosphates and a variety of compositions comprising synthetic and mineral oil based lubricants and greases and fuels into which said imidazoline salts have been incorporated.

DESCRIPTION OF SPECIFIC EMBODIMENTS

The novel additive products of this invention are generally prepared in the manner given below.

Long chain hydrocarbyl vicinal diols are (1) converted to their corresponding acid phosphates or partial acid phosphates by reaction with phosphorus pentoxide and (2) converted to the imidazoline, for example, salts of the acid phosphates by rection with various hydroxyalkyl imidazolines:

$$R^4(OH)_2$$

where $R^4$ is $C_8$–$C_{32}$ hydrocarbyl, or more preferred

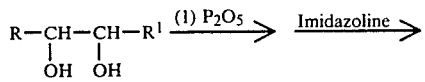

where $R = C_3$–$C_{30}$ hydrocarbyl, and $R^1 =$ hydrogen or $C_1$–$C_6$ hydrocarbyl.

Any suitable imidazoline may be used herein. Preferred are hydroxyalkyl hydrocarbyl imidazolines such as, for example

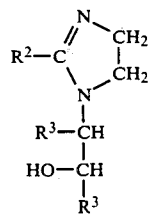

wherein $R^2$ is alkyl, alkenyl, cycloalkyl, cycloalkenyl, aryl, alkaryl, aralkyl of from about 5 to about 29 carbon atoms and $R^3$ is hydrogen or $C_1$–$C_6$ alkyl. Aryl ring components can contain from 6 to about 14 carbon atoms. The $R^2$-C grouping is often derived from linoleyl, oleyl, stearyl, isostearyl, hydrogenated tall oil, coco, dodecyl, or similar moieties or mixtures of similar groups. The described imidazolines may be readily obtained commercially or prepared in any convenient manner known to the art.

The diol, polyol or mixtures thereof are reacted with phosphorus pentoxide under ambient conditions or at temperatures of from about 50° to 150° C. Higher pressures may be used if desired. Conversion to the imidazoline salt is accomplished under essentially the same reaction conditions with 25–150% molar quantities.

Preferred diols include 1,2-dodecanediol, 1,2-tetradecanediol, 1,2-pentadecanediol, 1,2-hexadecanediol, 1,2-heptadecanediol, 1,2-octadecanediol, mixtures of such diols, and diols prepared by the hydrolysis of epoxides of propylene trimer, propylene tetramer, butylene trimers and tetramers and similar diols. The diol or polyol is converted to at least the partial acid phosphate by reaction with 5–100% molar quantities, and preferably 25–75% molar quantities of phosphorus pentoxide followed by at least partial conversion to the imidazoline salts by reaction with the appropriate heterocyclic compound.

In general, in most instances, the product is employed in an amount from about 0.1% to about 10% by weight, and preferably in an amount of from about 0.5% to about 5% by weight of the total weight of the composition. When used in fuels, the product may be present from about 0.00001 to about 1% by weight, preferably from about 0.001 to about 0.01% by weight. Of particular significance, is the ability of the additive products in such minor amounts to counteract the accelerating effect of oxidation on metal and on lubricant deterioration.

These products may be incorporated into either mineral or synthetic oils or mixtures thereof, or greases in which any of the aforementioned oils are employed as a vehicle. These compositions can also contain detergents and dispersants, as well as inhibitors, antiwear, extreme pressure, antifoam, pour depressant, and viscosity index improving additives or other additives for their known purposes without negating the beneficial properties of the novel compositions of the invention.

In general, mineral oils employed as the lubricant or grease vehicle may be of any suitable lubricating viscosity range, as for example, from about 45 SSU at 100° F. to about 6,000 SSU at 100° F., and preferably from about 50 SSU at 210° F. to about 250° SSU at 210° F. These oils may have viscosity indexes varying from below 0 to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease of formulation.

In instances where a synthetic oil or synthetic oils are employed as the vehicle for the grease, in preference to mineral oils, or in combination therewith, various components may be successfully utilized. Typically synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl)sebacate, di(2-ethylhexyl)adipate, di(-butylphthalate)fluorocarbons, silicate esters, silanes, esters of phosphorus-containing acids, liquid ureas, ferrocene derivatives, hydrogenated mineral oils, chain-type polyphenols, siloxanes and silicones(polysiloxanes), alkyl-substituted diphenyl ethers typified by a butyl-substituted bis(p-phenoxyphenyl)ether, phenoxy phenylethers, etc.

Greases in accordance with the present invention containing the above-described products, are prepared by combining an oil of lubricating viscosity with a grease-forming quantity of a thickening agent. For this purpose, a wide variety of materials may be employed. The thickening or gelling agents may include any of the conventional metal salts or soaps, which are dispersed in the lubricating vehicle in grease-forming quantities, in such degree as to impart to the resulting grease composition the desired consistency. Other thickening agents that may be employed in the grease formation may comprise the non-soap thickeners, such as surface modified clays and silicas, aryl ureas, calcium complexes and similar materials. In general, grease thickeners may be employed which do not melt and dissolve when used at the required temperature within a particular environment, however, in all other respects, any materials which are normally employed for thickening or gelling hydrocarbon fluids for forming grease, can be used in preparing the greases in accordance with the present invention.

Although the following examples specifically illustrate the invention, it is understood that they are meant to be illustrations and not limitations to the invention.

EXAMPLE 1

Partial Acid Phosphate of 1,2-Mixed-Pentadecanediol-Octadecanediol

Approximately 480 g of 1,2-mixed-pentadecanediol-octadecanediol (obtained commercially as Vikol 158 from Viking Chemical Company, and containing approximately 28% 1,2-pentadecanediol, 28% 1,2-hexadecanediol, 28% 1,2-heptadecanediol and 16% 1,2-octadecanediol) and 200 g hexane were charged to a 2 liter reactor equipped with agitator and condenser. The contents were warmed to about 60° C. and 70 g phosphorus pentoxide were slowly added over a period of two hours while maintaining a temperature of about 60°–70° C. The temperature was held for one hour at about 60° C. and raised to 100° C. for three additional hours. The remaining solvent was removed by distillation under reduced pressure.

EXAMPLE 2

Hydroxylalkyl Alkenyl Imidazoline Salt of Partial Acid Phosphate of 1,2-Mixed Pentadecanediol-Octadecanediol Approximately 135 g of the product of Example 1 was reacted with 175 g of 1-(2-hydroxyethyl)-2-heptadecenyl imidazoline for ½ hour at about 80° C. with agitation until reaction was complete.

EXAMPLE 3

Acid Phosphate of 1,2-Mixed-Pentadecanediol-Octadecanediol Concentrate in Process Oil Approximately 480 g of 1,2-mixed pentadecanediol-octadecanediol (as described in Example 1) and 200 g hexane were charged to a 2 liter reactor equipped with agitator and condenser. The contents were warmed to about 60° C. and 140 g phosphorus pentoxide were slowly added over a period of two hours. This temperature was maintained at about 60°–65° C. for one hour and then raised to about 100° C. for three additional hours. Approximately 200 g of 100 second solvent paraffinic neutral lubricating oil were added at this point as a diluent oil to reduce the distillation under reduced pressure.

EXAMPLE 4

Hydroxyalkyl Alkenyl Imidazoline Salt of Acid Phosphate of 1,2-Mixed Pentadecanediol-Octadecanediol concentrate in Process Oil Approximately 135 g of the product of Example 3 were reacted with 90 g of 1-(2-hydroxyethyl)-2-heptadecenyl imidazoline for ½ hour at about 80° C. with agitation until reaction was complete.

EXAMPLE 5

Partial Acid Phosphate of 1,2-Hexadecanediol

Approximately 480 g of 1,2-hexadecanediol and 100 g hexane were charged to a 2 liter reactor equipped with agitator and condenser. The contents were warmed to about 80° C. and 70 g phosphorus pentoxide were slowly added over a period of two hours while maintaining a temperature of about 80° C. The temperature was held at about 80° C. for one hour and then raised to 100° C. for three additional hours. The remaining solvent was removed by distillation under reduced pressure.

EXAMPLE 6

Hydroxyalkyl Alkenyl Imidazoline Salt of Partial Acid Phosphate of 1,2-Hexadecanediol Approximately 65 g of the product of Example 5 were reacted with 90 g of 1-(2-hydroxyethyl)-2-heptadecenyl imidazoline for ½ hour at about 80° C. with agitaion until reaction was complete.

The imidazoline derivatives of the acid phosphates were blended into fully formulated synthetic and mineral oil based engine oil lubricants and evaluated using the low Velocity Friction Apparatus Test. The formulations also included zinc dialkyl dithiophosphates, metallic sulfonates, metallic phenates, polymeric dispersants and polymeric viscosity index improving additives.

The use of only 1% of the product of Example 2 reduced the coefficient of friction by 41% as shown in Table 1. These additives are accordingly effective friction reducers.

EVALUATION OF PRODUCTS

Low Velocity Friction Apparatus

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12-13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed.

Freshly polished steel specimens are used for each run. The surface of the steel is parallel ground to 4-8 microinches.

The data obtained are shown in Tables 1 and 2. The percentages by weight are percentages by weight of the total lubricating oil composition, including the usual additive package. The data are percent decrease in friction according to:

$$\frac{(U_k \text{ of oil alone}) - (U_k \text{ of additive plus oil})}{(U_k \text{ of oil alone})} \times 100$$

The value for the oil alone would be zero for the form of the data shown in the Tables.

TABLE 1

Friction Test Results Using Low Velocity Friction Apparatus

| | Additive Conc. in Test Oil Weight % | % Reduction in Coefficient of Friction at 5 Ft/Min | 30 Ft/Min |
|---|---|---|---|
| Base Fluid A (fully formulated mineral oil based automotive engine oil containing detergent/dispersant/inhibitor performance package) SAE 10W40 | — | 0 | 0 |
| Example 2 - 1-(2-hydroxyethyl)-2-heptadecenyl imidazoline reaction product of partial acid phosphate of 1,2-mixed-pentadecanediol-octadenanediol | 1.0 | 41 | 27 |
| Example 4 - 1-(2-hydroxyethyl)-2-heptadecenyl imidazoline reaction product of acid phosphate of 1,2-mixed-pentadecanediol-octadecanediol | 1.0 | 35 | 25 |
| Example 6 - 1-(2-hydroxyethyl)-2-heptadecenyl imidazoline reaction product of acid phosphate of 1,2-hexadecanediol | 1.0 | 26 | 18 |

TABLE 2

Friction Test Results Using Low Velocity Friction Apparatus

| | Additive Conc. in Base Fluid Weight % | % Reduction in Coefficient of Friction at 5 Ft/Min | 30 Ft/Min |
|---|---|---|---|
| Base Fluid B (fully formulated synthetic engine oil containing detergent/dispersant/inhibitor performance package) SAE 5W30 | — | 0 | 0 |
| Example 4 - 1-(2-hydroxyethyl)-2-heptadecenyl imidazoline reaction product of acid phosphate of 1,2-mixed pentadecanediol-octadecanediol | 1.0 | 36 | 33 |

The above data clearly demonstrate that the use of imidazoline derivatives of acid phosphates in premium quality automotive and industrial lubricants significantly enhances the lubricants friction modifying characteristics. The novel compositions described herein are effective at low concentrations, are non-metallic and do not contain any potentially corrosive sulfur and provide an unexpected combination of friction reduction and antiwear activity.

It is understood by those of ordinary skill in the art that departure from the preferred emobidments described herein can be effectively made and that such departures are within the scope of the specification.

We claim:

1. A lubricant composition comprising a major amount of an oil of lubricating viscosity or grease prepared therefrom and a minor amount of an additive compound effective for providing friction reducing properties to said composition consisting essentially of an imidazoline salt of a diol-derived acid phosphate or mixtures of imidazoline salts of said diol-derived acid phosphates prepared by reacting said diol or polyol with 5% to 100% molar quantities of phosphorus pentoxide at temperatures of 50° to 150° C. followed by reacting the product thereof with an imidazoline in molar ratios of from about 0.25% to about 150%.

2. The composition of claim 1 wherein said diol or polyol described therein has the following generalized structure

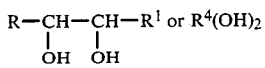

where $R=C_3-C_{30}$ hydrocarbyl, $R^1=$hydrogen or $C_1-C_6$ hydrocarbyl, and $R^4=C_8-C_{32}$ hydrocarbyl.

3. The composition of claim 1 wherein the imidazoline used to prepare said acid phosphate salt has the following generalized structure:

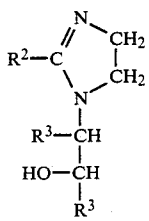

wherein $R^2$ is alkyl, alkenyl, cycloalkyl, cycloalkenyl, aryl, alkaryl or aralkyl of from about 5 to about 29 carbon atoms and $R^3$ is hydrogen or $C_1-C_6$ alkyl.

4. The composition of claim 1 wherein the additive compound described therein is the partial acid phosphate of 1-2-mixed pentadecanediol-octadecanediol and 1-(2-hydroxyethyl)-2-heptadecenyl imidazoline.

5. The composition of claim 1 wherein the additive compound described therein is the acid phosphate of 1-2-mixed pentadecanediol-octadecanediol and 1-(2-hydroxyethyl)-2-heptadecenyl imidazoline.

6. The composition of claim 1 wherein the additive compound described therein is the acid phosphate of 1-2-hexadecanediol and 1-(2-hydroxyethyl)-2-heptadecenyl imidazoline.

7. The composition of claim 1 wherein said oil is a mineral of synthetic oil or mixtures thereof.

8. The composition of claim 1 wherein said major proportion is a grease.

9. A method of reducing fuel consumption in internal combustion engines comprising treating the moving surfaces thereof with a lubricant composition as described in claim 1.

10. A compound prepared by reacting an imidazoline and the acid phosphate of a hydrocarbyl diol at temperatures of from about 50° to about 100° C. under suitable reaction conditions whereby the imidazoline salt of the acid phosphate or partial acid phosphate of hydrocarbyl diol is prepared and wherein said imidazoline is represented by the general formula

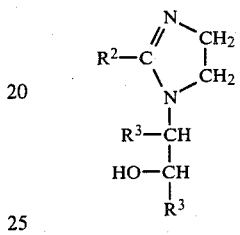

wherein $R^2$ is alkyl, alkenyl, cycloalkyl, cycloalkenyl, aryl, alkaryl, aralkyl of from about 5 to about 29 carbon atoms and $R^3$ is hydrogen or $C_1-C_6$ alkyl.

11. The compound of claim 9 wherein the compound is the 1-(2-hydroxyethyl)-2-heptadecenyl imidazoline reaction product of partial acid phosphate of 1-2-mixed pentadecanediol-octadecanediol.

12. A compound as described in claim 9 wherein the compound is the 1-(2-hydroxyethyl)-2-heptadecenyl imidazoline reaction product of acid phosphate of 1-2-mixed pentadecanediol-octadecanediol.

13. A compound as described in claim 9 wherein the compound is the 1-(2-hydroxyethyl)-2-heptadecenyl imidazoline reaction product of acid phosphate of 1-2-hexadecanediol.

* * * * *

UNITED STATES PATENT AND TRADEMARK OFFICE
CERTIFICATE OF CORRECTION

PATENT NO. : 4,661,271

DATED : April 28, 1987

INVENTOR(S) : Andrew G. Horodysky and Henry Ashjian

It is certified that error appears in the above-identified patent and that said Letters Patent is hereby corrected as shown below:

Col. 1, line 25, "Hydroxy-" should be --Hydroxyl- --.

Col. 1, line 67, "rection" should be --reaction--.

Col. 8, Claims 11, 12, 13, "9" should read -- 10 --.

Signed and Sealed this

Twenty-ninth Day of September, 1987

Attest:

DONALD J. QUIGG

Attesting Officer     Commissioner of Patents and Trademarks